(12) United States Patent
McKenna et al.

(10) Patent No.: US 7,721,930 B2
(45) Date of Patent: May 25, 2010

(54) DISPOSABLE CARTRIDGE WITH ADHESIVE FOR USE WITH A STAPLING DEVICE

(75) Inventors: Robert H. McKenna, Bountiful, UT (US); Frederick E. Shelton, IV, Hillsboro, OH (US); Randal T. Byrum, Kings Mills, OH (US); Mark S. Ortiz, Milford, OH (US); Paul J. Conrad, West Chester, OH (US); Eugene L. Timperman, Cincinnati, OH (US)

(73) Assignee: Thicon Endo-Surgery, Inc., Cincinnati, OH (US)

( * ) Notice: Subject to any disclaimer, the term of this patent is extended or adjusted under 35 U.S.C. 154(b) by 88 days.

(21) Appl. No.: 11/558,524

(22) Filed: Nov. 10, 2006

(65) Prior Publication Data

US 2008/0110958 A1    May 15, 2008

(51) Int. Cl.
*A61B 17/072* (2006.01)
(52) U.S. Cl. ............ 227/176.1; 227/175.1; 227/19
(58) Field of Classification Search ... 227/175.1–182.1, 227/19
See application file for complete search history.

(56) References Cited

U.S. PATENT DOCUMENTS

| | | | |
|---|---|---|---|
| 4,900,303 A * | 2/1990 | Lemelson | 604/514 |
| 5,928,611 A | 7/1999 | Leung | |
| 6,010,054 A * | 1/2000 | Johnson et al. | 227/176.1 |
| 6,024,480 A * | 2/2000 | Seaton et al. | 366/130 |
| 6,217,603 B1 | 4/2001 | Clark et al. | |
| 6,455,064 B1 | 9/2002 | Narang et al. | |
| 6,656,193 B2 * | 12/2003 | Grant et al. | 606/151 |
| 6,681,979 B2 * | 1/2004 | Whitman | 227/180.1 |
| 7,431,730 B2 | 10/2008 | Viola | |
| 2004/0007608 A1 * | 1/2004 | Ehrenfels et al. | 227/176.1 |
| 2004/0190975 A1 | 9/2004 | Goodman et al. | |
| 2005/0145671 A1 * | 7/2005 | Viola | 227/175.1 |
| 2005/0184121 A1 * | 8/2005 | Heinrich | 227/175.1 |
| 2005/0192628 A1 * | 9/2005 | Viola | 606/219 |
| 2006/0239359 A1 | 10/2006 | Savekar et al. | |

FOREIGN PATENT DOCUMENTS

WO   WO 03/088845   10/2003

OTHER PUBLICATIONS

U.S. Appl. No. 09/430,177, filed Oct. 29, 1999, Narang et al.

* cited by examiner

*Primary Examiner*—Rinaldi I. Rada
*Assistant Examiner*—Lindsay Low
(74) *Attorney, Agent, or Firm*—Frost Brown Todd LLC

(57) ABSTRACT

A surgical stapling device is provided for clamping and stapling tissue, and for dispensing a fluid such as an adhesive onto the tissue. The adhesive can be stored within one or more rigid chambers within removable cartridge and dispensed from a plurality of passageways within the cartridge. A plurality of staples and staple drivers are located in the cartridge and may be isolated from the fluid. Both linear and rotary members can be provided to dispense the fluid from the cartridge. Alternately, the fluid can be dispensed from the cartridge at any time with an operator actuatable control. A removable staple cartridge cover can be provided to seal the fluid in the cartridge and prevent fluid loss. Alternately, a fluid cartridge can be provided that can mount within a surgical stapling device and dispense one or more firings of a fluid therefrom.

14 Claims, 16 Drawing Sheets

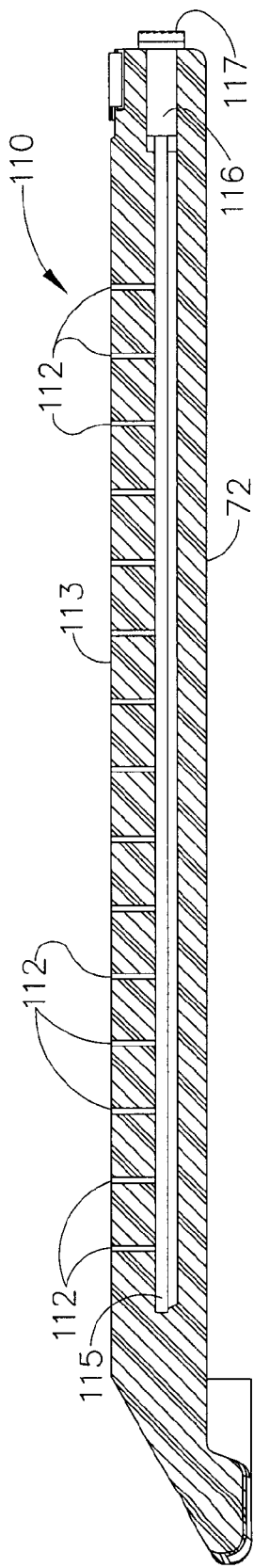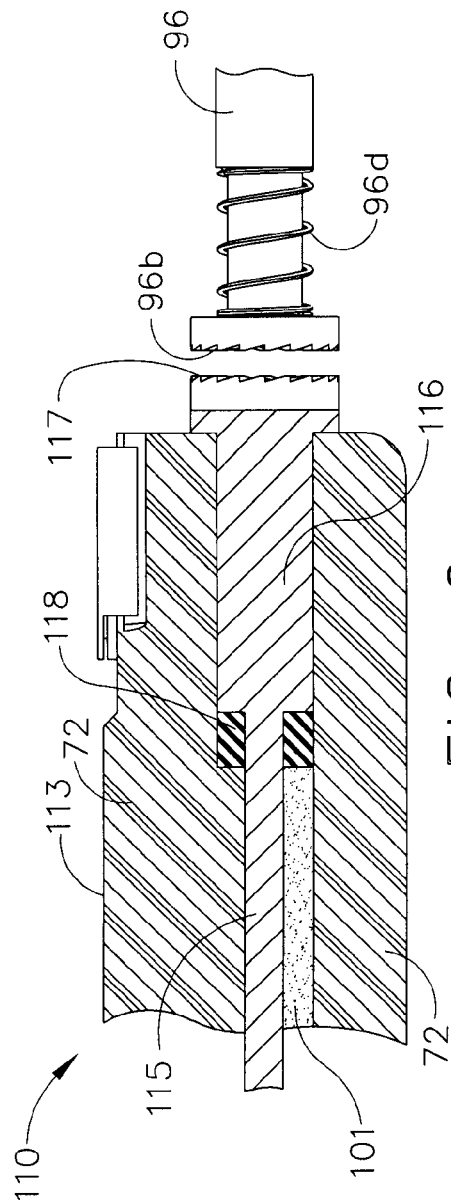

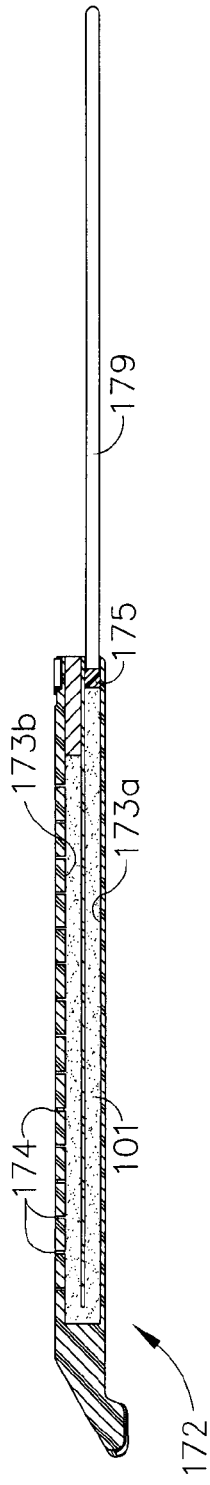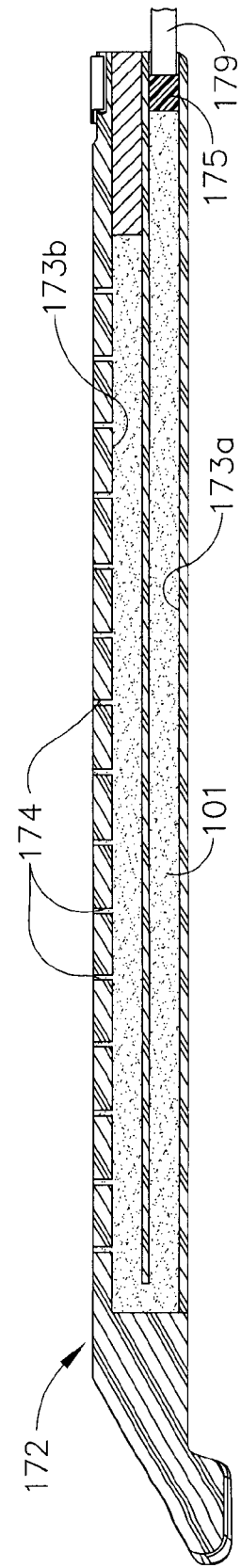

DISPOSABLE CARTRIDGE WITH ADHESIVE FOR USE WITH A STAPLING DEVICE

FIELD OF THE INVENTION

The present invention relates, in general, to surgical stapling devices, and to surgical stapling devices with a disposable cartridge containing staples and glue

BACKGROUND OF THE INVENTION

Adhesives and sealants have been contemplated to supplement or replace staple based transaction devices for many years. The primary challenges in accomplishing this are control of getting the adhesive into the correct location at the correct time as well as preventing it from adhering the stapler itself to the treatment site. Adhesives have proven themselves as great short term bonding/sealing mechanisms. Staples on the other have proven themselves a very good long term tissue apposition mechanisms. Therefore the best of both worlds would be to use staples to fasten and adhesives in combination with adhesive initiators to seal the juncture of tissue or tissue cuts.

The primary challenge in the creation of a hybrid adhesive/staple deploying system is the positioning of the adhesive into only the areas of desired adhesion and controlling where the adhesive bonds to the area.

Closure Medical is conducting an FDA clinical trial using a cyanoacrylate adhesive as an internal vascular tissue sealant and internal surgical adhesive. Some adhesives such as the cyanoacrylates, stick well to tissue, but like metallic fasteners, the fastener itself can become a local barrier to tissue regrowth through the fastener. For internal body use of surgical adhesives, the adhesive is used sparingly, not on top of the wound as in external use, but actually in the cut areas of the wound. By minimizing the glue areas across the wound, the surgeon is assured of maximum areas of tissue regrowth and minimal areas of the adhesive barrier. As the tissue regrows together and heals, the adhesive areas within the wound are encapsulated with healed tissue. Thus, internal adhesives are ideal for short term needs to hold cut tissue together so that healing can occur, and can remain as a long term fastener to provide additional strength to the healed tissue. Additionally, the adhesives can be biocompatable, bioabsorbable, and/or flexible, inside the body.

Tissue fastening can be either short term or long term duration. Short term duration fasteners can include a bandage, tape, removable staples, removable suture, adhesives, or absorbable stitches that are meant to provide temporary support until natural healing can occur.

Longer duration fasteners must remain in or on the body, possibly for the life of the patient. Longer duration fasteners include biocompatible implantables such as suture, staples, clips, tacks, clamps, pins, and the like. These long duration fasteners could be inserted subcutaneously in a surgical procedure and, after the patient has healed, cannot be removed without additional surgery. Longer term fasteners can provide short term and long term reinforcement for high force loads that can be 200-400% of normal forces. These high force loads could be caused by violent vomiting, coughing, and, in some cases, chronic overeating. For chronic overeaters that have undergone bariatric surgery to create a small stomach pouch, it is highly likely that a patient will "overload" the new pouch by attempting to eat the same large portions of food imbibed before the surgery.

Adhesives have been used topically as a short term fastener for wound repair. Closure Medical has developed a 2-octyl cyanoacrylate compound with a long carbon chain (eight carbons) that is biocompatible, has good bonding strength, and has received FDA approval for topical use. For short duration topical wound closure, the edges of the wound are brought together and at least one layer of the adhesive is applied along the surface of the wound line to form a barrier that holds the wound edges together. The cyanoacrylate adhesive also acts as a microbial barrier, keeping bacteria out and is eventually removed. Cyanoacrylate adhesives are described in U.S. application 20040190975 by Goodman et al. which is herein incorporated by reference in its entirety.

Closure Medical is conducting an FDA clinical trial using a cyanoacrylate adhesive as an internal vascular tissue sealant and internal surgical adhesive. Some adhesives such as the cyanoacrylates, stick well to tissue, but like metallic fasteners, the fastener itself can become a local barrier to tissue regrowth through the fastener. For internal body use of surgical adhesives, the adhesive is used sparingly, not on top of the wound as in external use, but actually in the cut areas of the wound. By minimizing the glue areas across the wound, the surgeon is assured of maximum areas of tissue regrowth and minimal areas of the adhesive barrier. As the tissue regrows together and heals, the adhesive areas within the wound are encapsulated with healed tissue. Thus, internal adhesives are ideal for short term needs to hold cut tissue together so that healing can occur, and can remain as a long term fastener to provide additional strength to the healed tissue. Additionally, the adhesives can be biocompatable, bioabsorbable, and/or flexible, inside the body.

Staple cartridges containing fluids such as an adhesive are described in International publication WO03088845-A2 by R. Heinreich which is hereby incorporated by reference in its entirety.

Consequently, a significant need exists for a surgical stapling device that has a removable staple cartridge that contains and dispenses a fluid such as an adhesive from one or more rigid and/or non-frangible compartments within the cartridge, that the one or more adhesive compartments are separate from and away from the staples and drivers, and the fluid can be dispensed onto tissue at any time before, during or after one or more of clamping, cutting, and stapling.

BRIEF SUMMARY OF THE INVENTION

The invention overcomes the above-noted and other deficiencies of the prior art by providing a surgical stapling device for clamping and stapling tissue. The surgical stapling device having a first clamping jaw and a second clamping jaw extending from a distal end of the shaft to clamp tissue therebetween. The second clamping jaw is movable from an open position for the reception of tissue to a closed position to clamp tissue between the first clamping jaw and the second clamping jaw. A removable cartridge is mounted in the first clamping jaw and has a tissue clamping surface thereon. The removable cartridge contains a plurality of staples and staple ejection members therein, a fluid, and a fluid dispensing system for dispensing the fluid from the clamping surface of the removable cartridge. The fluid dispensing system has at least one rigid chamber with a movable member therein and a plurality of rigid fluid passageways operably connecting the at least one rigid chamber with the tissue clamping surface. The at least one rigid chamber and the plurality of rigid fluid passageways contain the fluid therein and keep the fluid separate from contact with the plurality of staples and staple ejection members.

A firing system is located within the surgical stapling device and has a translating member that operably couples with the staples and staple ejection members. When the firing system is actuated, the plurality of staples are ejected from the removable cartridge into clamped tissue and formed against the second clamping jaw.

And a fluid dispensing system is least partially contained within the shaft and operably coupled with the movable member in the removable cartridge when the removable cartridge is mounted in the first clamping jaw. Wherein when the fluid dispensing system is actuated, the movable member is moved and fluid is dispensed from the removable cartridge onto tissue.

In another aspect of the invention, a removable fluid cartridge is provided for use in a surgical stapling device for clamping and firing on tissue. The removable fluid cartridge comprises a fluid cartridge body having a tissue clamping surface and a plurality of passageways operably connecting a hollow chamber within to the tissue clamping surface. A fluid is located within the at least one chamber and the plurality of passageways of the fluid cartridge body. And, a fluid dispensing system is located within the cartridge body for dispensing the fluid from the plurality of passageways. Wherein when the fluid cartridge is installed into the surgical stapling device, the adhesive dispensing system is operably coupled with a staple firing system of the surgical stapling device such that firing the surgical stapling device dispenses the fluid onto tissue from the plurality of passageways.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 8 is a side cross sectional view of a staple cartridge of FIG. 1 showing a fluid, the first fluid application system and adhesive channels for dispensing the fluid such as an adhesive therefrom.

FIG. 9 is a side cross sectional view of the staple cartridge of FIG. 8 showing a dog clutch drive system to dispense fluid from the first fluid application system just prior to connecting the dog clutches.

FIG. 14 is a side cross sectional view of a staple cartridge of FIG. 10 showing the fluid, the second fluid application system and adhesive channels for dispensing the fluid such as an adhesive therefrom.

FIG. 15 is an enlarged partial side cross sectional view of a staple cartridge of FIG. 14.

DETAILED DESCRIPTION OF THE INVENTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
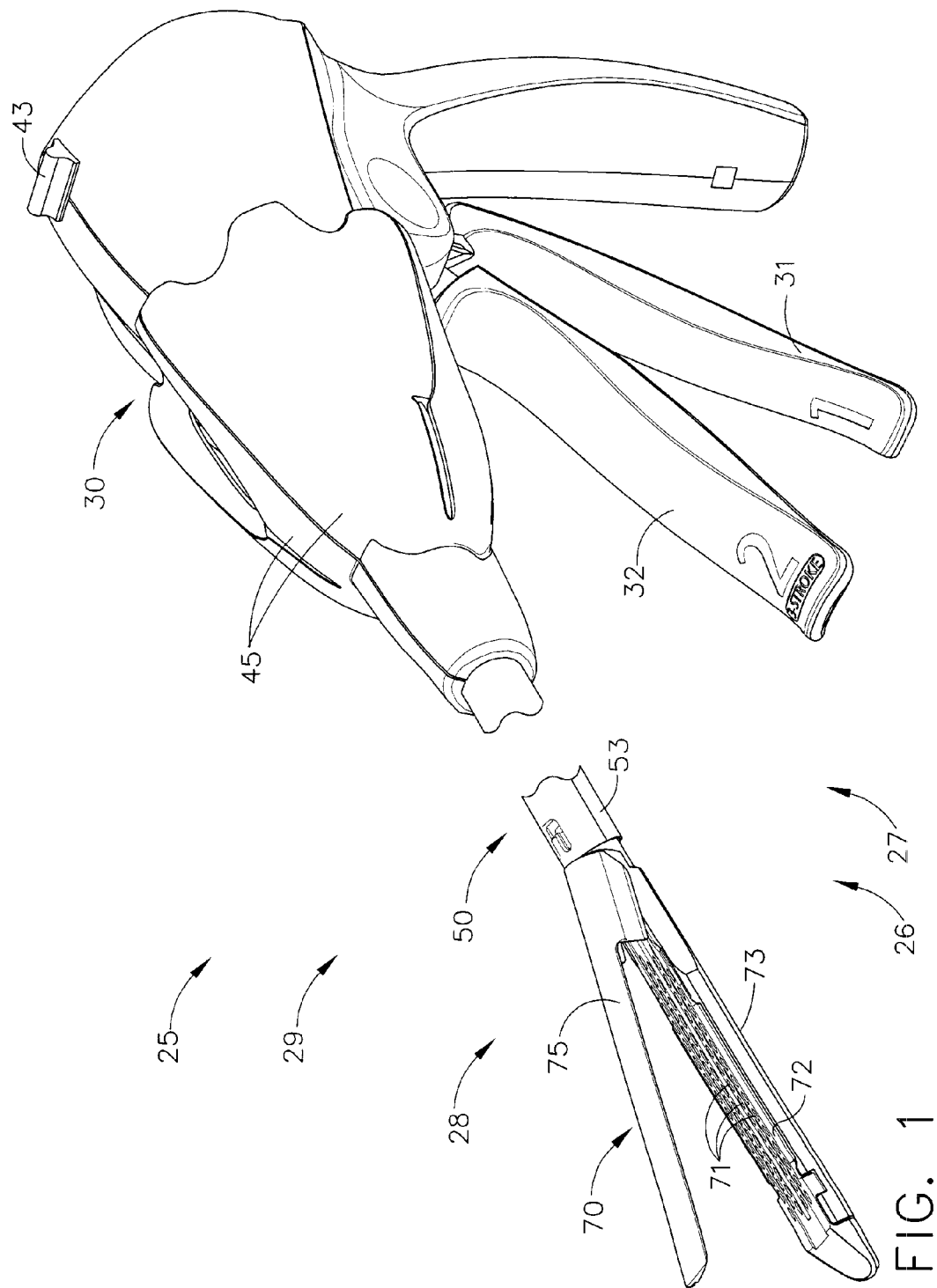
FIG. 1 is an isometric view of a surgical device for clamping, stapling, and cutting tissue, with a fluid application system for dispensing fluid onto tissue.

An endoscopic surgical stapling device is shown in FIG. 1. The surgical device 25 has a handle 30, a shaft assembly 50 extending therefrom including an end effector 70. Surgical device 25 can contain a clamping system 26 for clamping tissue, and a firing system 27 for firing a plurality of staples 71 from a removable cartridge 72 located within the end effector 70 into tissue. The firing system 27 also can cut clamped and stapled tissue within the end effector 70. A frame assembly 28 has a fluid application system 29 for dispensing a fluid 100 from the replaceable or removable cartridge 72 onto tissue clamped within the end effector 70 can also be provided. The dispensable fluid 100 can be any one of a number of fluids, but for this example will be an adhesive 101

The clamping system 26 can clamp tissue with the end effector 70 between a fixed jaw 73 containing the staples 71 in staple pockets 72a (not shown) in cartridge 72, and a movable jaw or anvil 75. A clamping trigger 31 could be pivotally mounted in handle 30 and operably coupled to the anvil 75 such that actuation of closure trigger 31 moves anvil 75 from the open position of FIG. 5 to a closed position of FIG. 6.

Actuation of firing trigger 32 may eject the plurality of staples 71 from the cartridge 72, form the staples 71 against the anvil 75, and advance a knife 76 (FIG. 3) longitudinally between the fixed jaw 73 and the cartridge 72 to cut the tissue clamped therebetween. The adhesive 101 could be contained within substantially rigid chambers the removable cartridge 72 and may be dispensed by the fluid application system 29 onto the clamped, stapled and cut tissue between fixed jaw 73 and the anvil 75.

Figure 2:
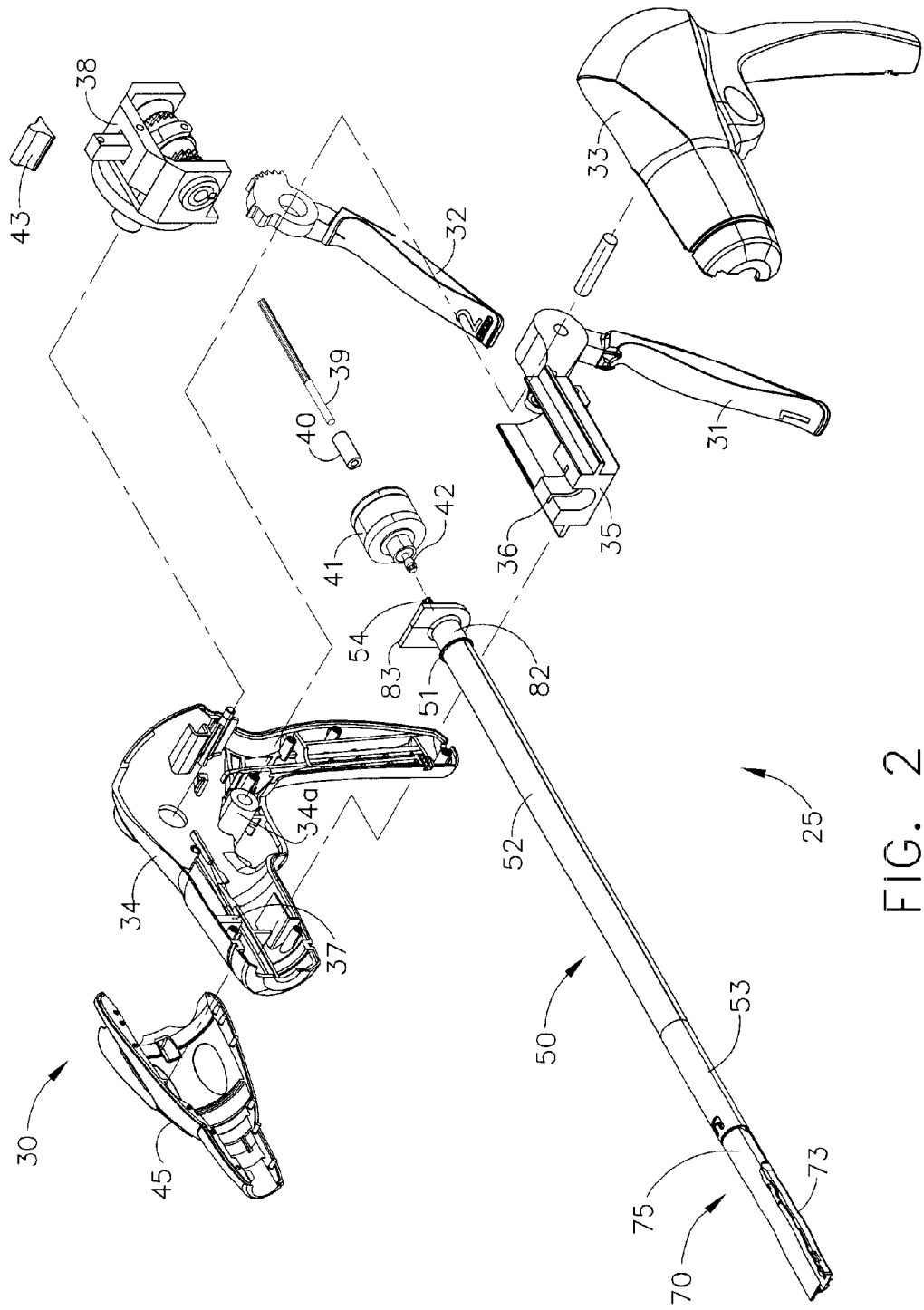
FIG. 2 is an isometric exploded view of a handle of the surgical device of FIG. 1 with an unexploded shaft assembly.

FIG. 2 is a partially exploded view of the surgical device 25 showing the handle 30 exploded about the assembled shaft assembly 50. Handle 30 could have a left shroud 33 and a right shroud 34 that assemble together. Clamping trigger 31 can rotatably mount on a boss 34a and be pivotally linked to a yoke 35 that slidingly mounts in handle 30 such that actuation of clamping trigger 31 moves yoke 35 longitudinally in shrouds 33, 34 of handle 30. A slot 36 can be provided in the yoke 35 for the reception of a flange 51 of a closure tube 52 to move closure tube 52 distally and proximally to close and open anvil 75. A frame slot 37 can be located in left shroud 33 and right shroud 34 for the fixed reception of a frame flange 83 of the shaft assembly 50. The frame slot 37 may be operably coupled to the fixed jaw 73 to hold fixed jaw 73 fixed longitudinally to handle 30. A split rotary knob 45 can be provided to attach to and rotate the shaft assembly 50 relative to handle assembly 30. One half of split rotary knob 45 is removed for clarity.

The firing system 27 could be a multi-stroke firing system using multiple strokes of the firing trigger 32 to fire the staples from the cartridge, and to cut the stapled tissue. The firing trigger 32 could be operably coupled to a rotation gearbox 38 such that rotary actuation of the firing trigger 32 is converted to rotary motion about the longitudinal axis of the surgical device 25 by the rotation gearbox 38. A reverse lever 43 may provided to reverse direction of the rotation from actuation of firing trigger 32. A splined drive 39 could be rotatingly and slidingly received in received in rotation gearbox 38 to operably couple rotation gearbox 38 to a secondary gearbox 41. The secondary gearbox 41 can be is attached to yoke 35 and move therewith in response to actuation of the clamping system 26. The splined drive 39 could be the input shaft for the secondary gearbox 41 and attached to secondary gearbox 41 with a coupler 40. Rotary output from secondary gearbox 41 can be coupled to the shaft assembly 50 by the operatively coupling of secondary coupler 42 to a drive spline 54 of shaft assembly 50.

Figure 3:
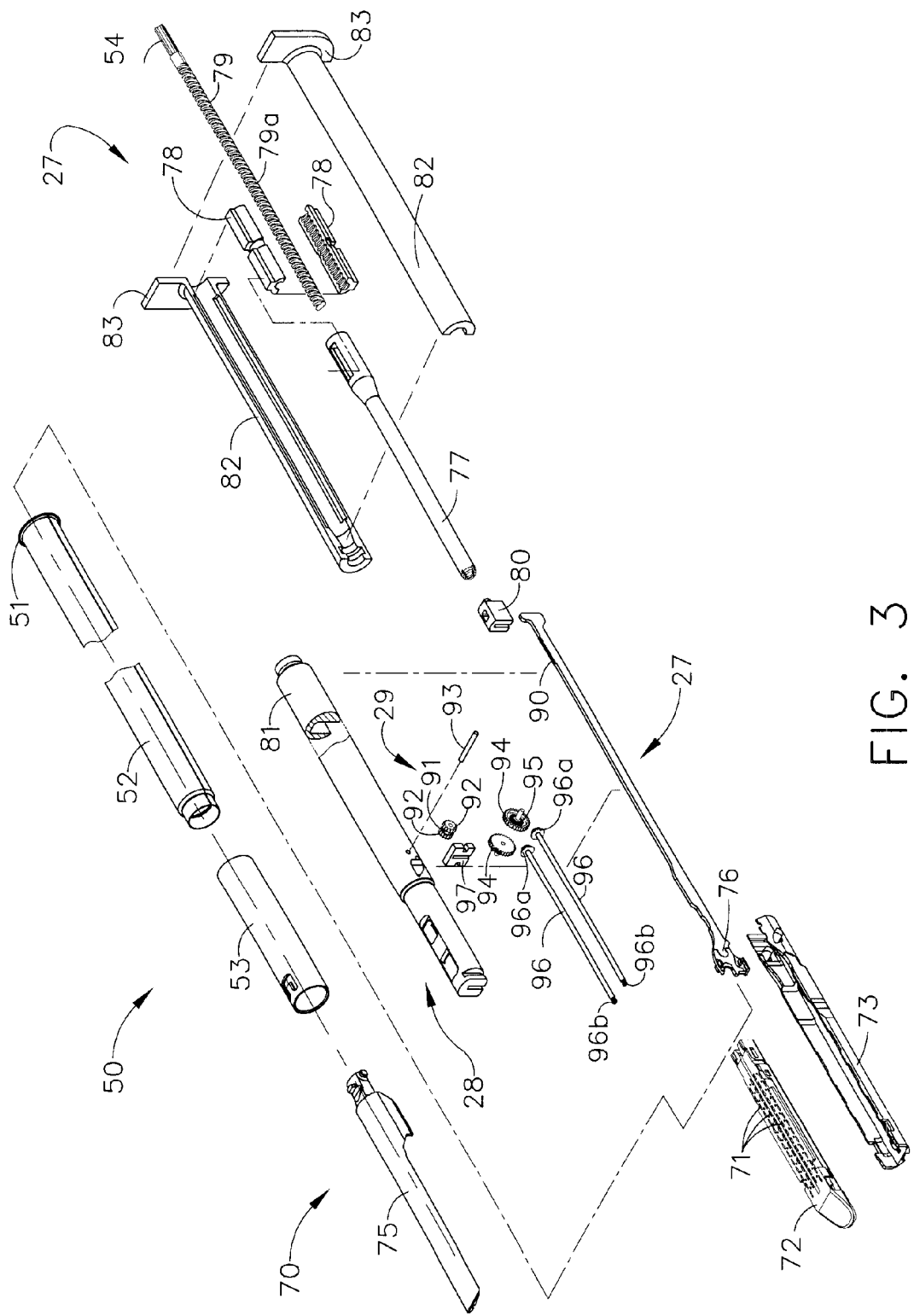
FIG. 3 is an isometric exploded view of the shaft assembly showing the fluid application system elements.

FIG. 3 shows an exploded view of the shaft assembly 50 and the end effector 70. The lower jaw 73 of the end effector 70 may be fixedly attached to the handle 30 by a fixed frame assembly 28. The fixed frame assembly 28 could have a distal frame portion 81 attached to and extending proximally from the fixed jaw 73. A split proximal frame portion 82 could capture the proximal end of distal frame portion 81 therebetween and may have flanges 83 captivated by handle shrouds 33, 34 to lock or fix the fixed frame assembly 28 relative to the handle 30.

The clamping mechanism 26 operably can couple the anvil 75 to the closure trigger 31 of the handle 30 to close anvil 75 when closure trigger 31 is actuated or closed, and to open anvil 75 when closure trigger 31 is moved to the open position of FIG. 1. Clamping mechanism 26 may extend into shaft assembly 50 and have a longitudinally moving closure tube 52 with previously described closure ring 51, and a distal closure ring 53 to push and pull on anvil 75. Distal movement of closure tube 52 and closure ring 52 pushes anvil 75 distally to close and proximal movement of closure tube 51 and closure ring 52 pulls anvil 75 proximally to open.

The firing system 27 could extends from firing trigger 32 in handle 30 and into shaft assembly 50. As described previously, a drive spline 54 of the firing system 27 can operatively engage in secondary coupler 42 in handle 30. Drive spline 54 may be located at a proximal end of a screw shaft 79. A split coupler block 78 can mount onto a threaded portion 79a of screw shaft 79 and move longitudinally in response to rotational input at drive spline 54. A longitudinally movable firing shaft 77 can fixedly mount about split coupler block 78 and operably attach to a knife 76 by a coupler block 78. Thus, drive spline 54 may be operably coupled to firing trigger 32 such that closure of firing trigger 32 moves knife 76 distally and opening movement of firing trigger 32 moves knife 76 proximally.

The fluid application system 29 can dispense any fluid 100 from the cartridge 72. For this example, an adhesive 101 is stored into cartridge 72 onto cut and stapled tissue. Adhesive 101 may used to seal leaks or bleeders at cut lines and about staples to provide additional strength to the stapled tissue. For this example, a fluid dispensing system such as a rotary mechanism can be located in cartridge 72 and rotates therein to dispense the adhesive 101. The rotary mechanism in the cartridge 72 will be described in detail later, but the elements of the fluid application system 29 in the shaft 50 and end effector 70 will now be discussed as shown in FIGS. 3-6.

Figure 4:
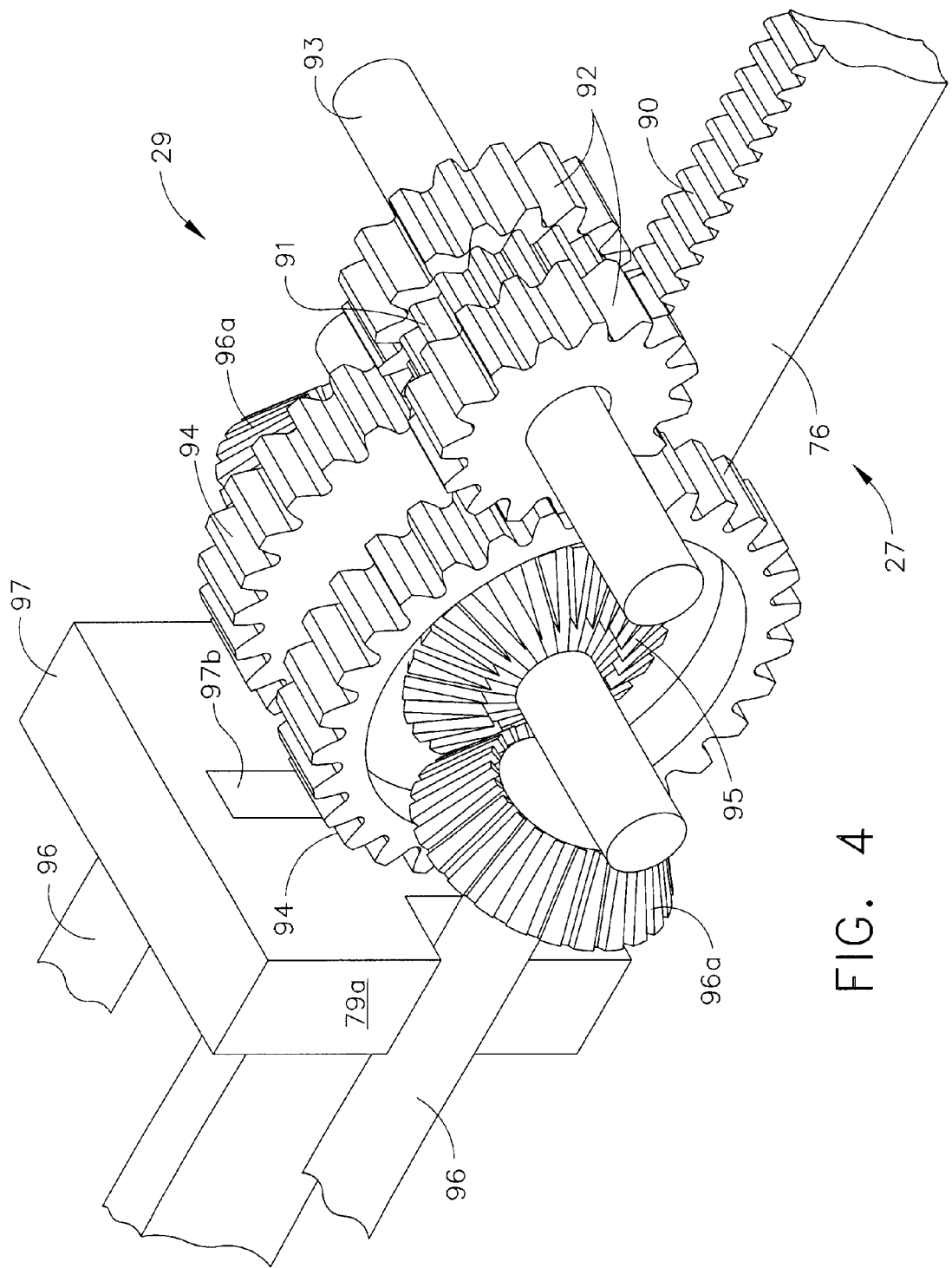
FIG. 4 is an isometric view of assembled elements of a drive mechanism of the fluid application system of FIG. 3.

In FIGS. 3 and 4, the fluid application system 29 can have a gear rack 90 on the top of longitudinally movable knife 76. A center gear 91 and attached drive gears 92 could be rotatably fixed in distal frame portion 81 by a pin 93, and gear 91 that operably engages with the gear rack 90 to rotate the gears 91, 92 in response to longitudinal movement of knife 76. A pair of separate shaft gears 94 can mount in slots (not shown) in distal frame portion 81 and are in driven engagement with the drive gears 92. Within each shaft gear 94 is a center bevel gear 95 can be attached thereon which rotate with the shaft gears 94. A pair of drive shafts 96 could extend longitudinally parallel to knife 76 and have drive bevels 96a at a proximal end and a drive dog clutch 96b at a distal end. Drive shafts 96 can rotatably mount within drive slots 97a in a shaft block 97 that fixedly mounts in distal frame 81. A knife slot 97b may be provided in shaft block 97 to guide knife 76 during proximal and distal motion.

Figure 5:
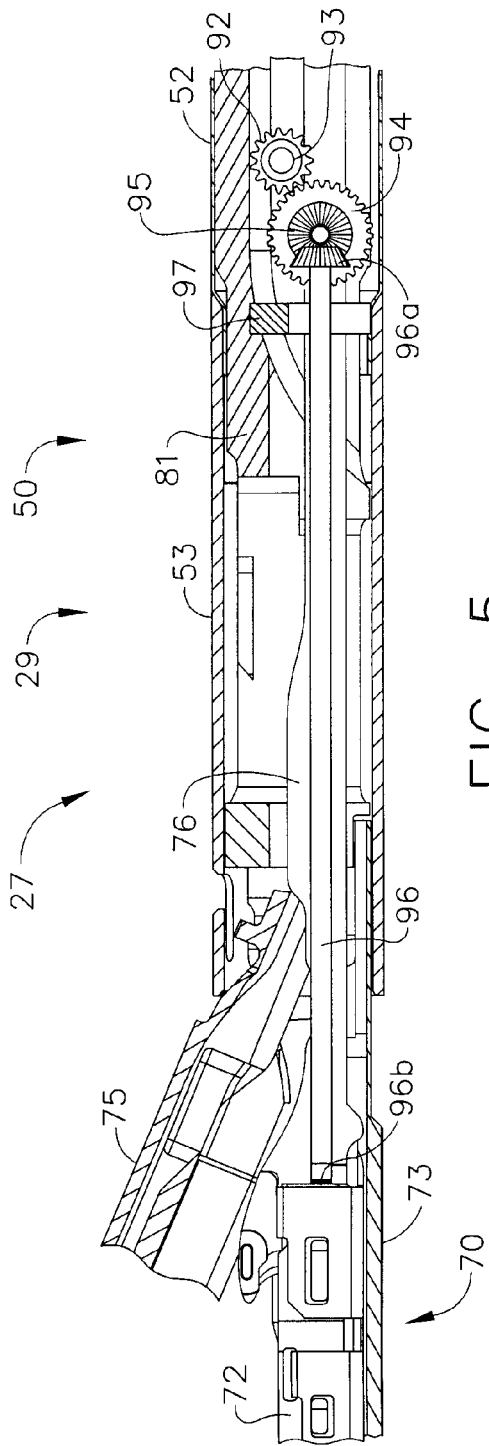
FIG. 5 is a cross sectional side view of the shaft assembly of FIG. 1 before clamping, cutting, stapling, and applying fluid.
Figure 6:
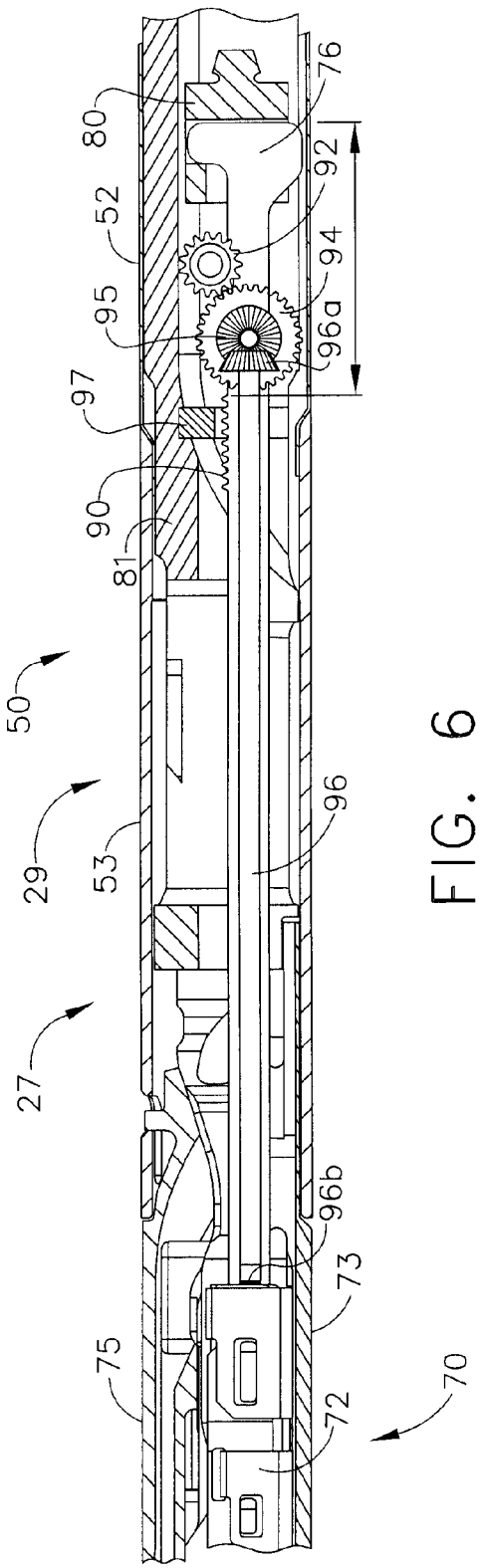
FIG. 6 is a cross sectional side view of the shaft assembly of FIG. 1 after clamping, cutting, stapling and applying fluid to tissue.

FIGS. 5 and 6 show the operation of the elements above of the fluid application system 29. In FIG. 5, the knife 76 is in the proximal most position, the anvil 75 is open for the receipt of tissue, and the drive shafts 96 may be engaged with an adhesive dispensing system 110 in the cartridge 72.

In FIG. 6, the anvil 75 is closed by distal movement of the closure ring 53 and closure tube 52. The firing system has been actuated and moved knife 76 distally to form the staples, to cut tissue within the jaws (not shown) and to actuate the fluid application system 29 by moving gear rack 90 distally to engage with the gear 91, rotate gears 92, 93, 95, 96a, and rotate drive shafts 96 to drive adhesive 101 from cartridge 72. Note that the gear rack 90 could be located a distance 98 from a proximal end of the knife 76. This distance 98 could engage the fluid application system 29 to dispense the adhesive 101 near to the end of the firing stroke, or at any point in the stroke. Making distance 98 longer can result in the adhesive being released sooner. Thus, fluid application system 29 can be tuned to apply adhesive 101 at any portion of the firing stroke.

Figure 7:
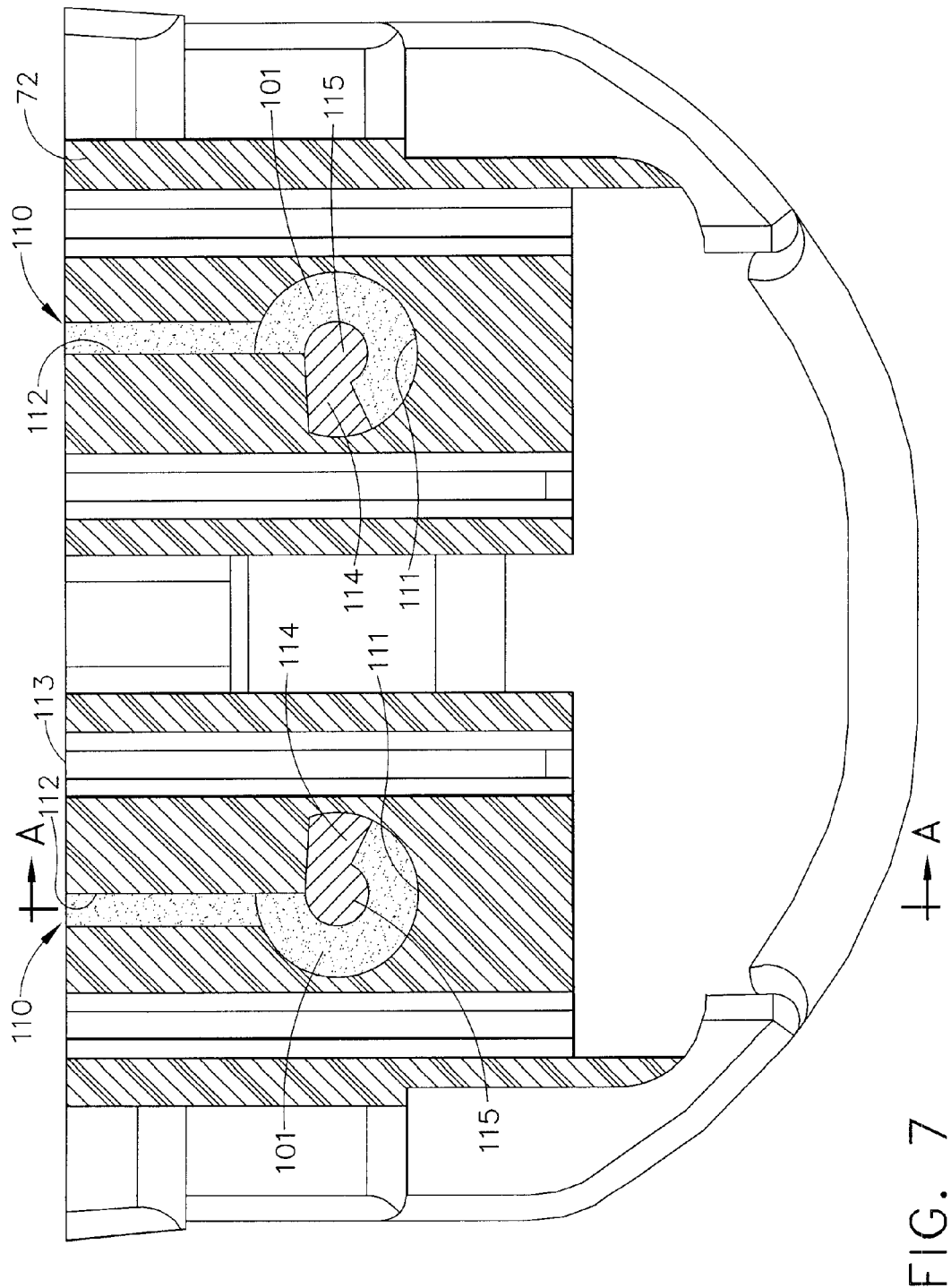
FIG. 7 is a cross sectional end view of a staple cartridge of FIG. 1 showing a fluid and a first fluid application system therein.

FIGS. 7-9 show the replaceable cartridge 72 having the adhesive dispensing system 110 therein. FIG. 7 is a cross sectional view of cartridge 72 showing the glue dispensing system 110 therein. Adhesive dispensing system 110 can comprise one or more cylindrical adhesive chambers 111 extending longitudinally through cartridge 72 and can include a plurality of adhesive channels 112 extending from one or more of the adhesive chambers 110 to a tissue clamp surface 113 of the removable cartridge 72. As shown, both the adhesive chambers 111 and the adhesive channels 112 may be filled with adhesive 101. A rotatable wiper blade 114 could be located in each of the adhesive chambers 111 such that rotation of wiper blades 114 pushes adhesive 101 from the adhesive chambers 111 and out of the plurality of adhesive channels 112.

FIG. 8 is a longitudinal cross section of cartridge 72 across section AA. The adhesive chamber 111 is shown sectioned as are the plurality of adhesive channels 112. The rotatable wiper blade 114 can have a shaft 115 extending longitudinally with a proximal drive shaft 116 at a proximal end of the cartridge 72. A seal 118 may prevent leakage of fluids 100 such as adhesive 101 about shaft 115. Dog clutch 96b can be located at a proximal end of the drive shaft 116. As shown in the partial cross section of FIG. 9, when the cartridge 72 is inserted into fixed jaw 73, the teeth of dog clutch 117 can be brought into operative engagement with the mating drive clutches 96b of the drive shaft 96 of the fluid application system 29. The dog clutches 96b can slide in and out of drive shaft 96 and are keyed to rotate with the drive shaft 96. Springs 96d are provided to ease engagement of cartridge 72 with drive shafts 96, to force the dog clutches 96b into engagement with the dog teeth 117 of the cartridge 72, and to accommodate rotary mismatch between the dog teeth 117 and the dog clutches 96b. Whereas a dog clutch system is used as an example, the present disclosure is not limited to dog clutches alone.

Removable Cartridge Cover

Whereas it is not shown, it is well known in the art that a removable cartridge cover can also be included with any stapling cartridge to prevent the dislodgement of fasteners from the cartridge. The covers are commonly removed in the operating room just prior to placement of the cartridge in the surgical stapling device 25. It is well within the scope of the present invention to include a cartridge cover 300 that can removably attach to a staple cartridge such as cartridge 72, can prevent the loss of staples 71, and may also have a seal 301 that covers the adhesive channels 112 to prevent egress or evaporation of fluids 100, 101 from the cartridge 72. The cartridge cover 300 can be generally rigid or flexible and may include an adhesive 302 that adheres to the cartridge 72. The adhesive can be a removable or peal-off adhesive 303, and can also act as a seal to prevent egress of the fluids 100, 101 within the cartridge. A flexible rubber-like material can also be used as the seal 301, or cover 300 and can be meltable from body contact to open adhesive channels 112.

Additionally, the seal or cover could be an absorbable cartridge cover 304 made from material that is a meltable or rapidly dissolving film such as those used for breath strips. Absorbable materials that could melt or dissolve or liquefy can include materials such as but are not limited to whey protein, cellulose gums, starches, gelatins, or other compounds. The absorbable cartridge cover 304 could be both a seal and a cover, can be placed onto tissue, and could be dissolved by body moisture, by the application of saline, by the application of an adhesive initiator, or by the application of any one of a number of other chemicals or compounds. If desired, removable cartridge cover 300 could be pouch, could be unsealed, sealed, and could be constructed from a sealing material that is removable or meltable.

The removable cartridge covers 300, 304 and seals 301 are not limited to the examples above and any other means used to prevent loss of fluid from passageways, can be used with any shape cartridge or fastener array such as circular, and alternate examples are well within the scope of the invention. Additionally, alternate compounds such as those described below can be used with absorbable cartridge cover 304.

Fluids for the Cartridge

In the above example, fluids 100 are an adhesive 101. Adhesives 101 could be, but are not limited to polymerizable and/or cross-linkable materials such as a cyanoacrylate adhesive. The adhesive 101, for example, may be a monomeric (including prepolymeric) adhesive composition, a polymeric adhesive composition, or any other compound that can adhere to tissue. In embodiments, the monomer may be a 1,1-disubstituted ethylene monomer, e.g., an .alpha.-cyanoacrylate. When cross linked or polymerized, the cyanoacrylate can change from a liquid to a solid. Polymerized adhesives 48a for example, can be formulated to be flexible to rigid. If desired, adhesive 48 an be a single part or dual part adhesive, and/or can contain additives such as alternate compounds 103. Polymerization of the adhesive 101 can occur from, but is not limited to, exposure to moisture or adhesion initiators. Adhesive 101 can also be mixed with other compounds or used neat.

Alternately, fluids 100 can be or include drugs, medicaments, contrasting agents, or any other compounds 103, neat, or any combination thereof. Examples of alternate compounds 103 can include, but are not limited to: adhesive initiators, image enhancing agents, necrosing agents, sclerosing agents, coagulants, therapeutic agents, medicaments, analeptic agents, anesthesia agents, antidiuretic agents, analgesic agents, antiseptic agents, antispasmodic agents, cardiac agents, depressant agents, diuretic agents, hemostatic agents, hormonal agents, sedative agents, stimulant agents, vascular agents, time release agents, drugs, absorbable materials (see below, colorants, plasticizing agents, bulking agents, tamponade materials, thixotropic agents, antibacterial agents, buffers, catalysts, fillers, micro particles, thickeners, solvents, natural or synthetic rubbers, stabilizers, pH modifiers, bioactive agents, cross-linking agents, chain transfer agents, fibrous reinforcements, colorants, preservatives, formaldehyde reducing or scavenging agents, flavorants, perfumes.

Adhesive initiators 104 are for polymerization and/or cross-linking of a polymerizable monomer. As used herein, a polymerization initiator is any material that causes a monomer composition applied to a substantially dry tissue (i.e., substantially in the absence of plasma or like tissue fluids) to polymerize in less than 300 seconds at ambient temperature, for example, at approximately 21-25.degree. C. Preferably, the initiator causes the monomer composition to polymerize in less than 150 seconds at ambient temperature, more preferably within 60, 90 or 130 seconds. As used herein, a polymerization rate modifier is any material that changes the rate at which a polymerizable monomer would polymerize in the absence of that material. Preferably, the rate modifier accelerates the rate of the polymerization reaction, although for particularly fast-acting monomers it may decelerate that rate.

Particular initiators 104 for particular monomers may be readily selected by one of skill in the art without undue experimentation. Control of the molecular weight distribution of the applied adhesive can be enhanced by selection of the concentration and functionality of the initiator or accelerator vis-a-vis the selected monomer. Suitable polymerization initiators and accelerators for cyanoacrylate compositions include, but are not limited to, detergent compositions; surfactants, including nonionic surfactants such as polysorbate 20 (e.g., Tween 20™; ICI Americas), polysorbate 80 (e.g., Tween 80™; ICI Americas), and poloxamers; cationic surfactants such as tetrabutylammonium bromide; anionic surfactants, including quaternary ammonium halides such as benzalkonium chloride or its pure components, and benzethonium chloride; stannous octoate (tin (II) 2-ethylhexanoate), and sodium tetradecyl sulfate; and amphoteric or zwitterionic surfactants such as dodecyldimethyl(3-sulfopropyl) ammonium hydroxide, inner salt; amines, imines, and amides, such as imidazole, tryptamine, urea, arginine and povidine; phosphines, phosphites and phosphonium salts, such as triphenylphosphine and triethyl phosphite; alcohols such as ethylene glycol; methyl gallate; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat™ 336 (General Mills, Inc., Minneapolis, Minn.); organometallics; manganese acetylacetonate; radical initiators and radicals, such as di-t-butyl peroxide and azobisisobutyronitrile; and bioactive compounds or agents.

Alternately, the initiator may be a bioactive material, including quaternary ammonium halides such as alkylbenzyldimethylammonium chloride (benzalkonium chloride; BAC) its pure components, or mixtures thereof, especially those with an alkyl containing 6-18 carbon atoms; benzethonium chloride; and salts of sulfadiazine. Cobalt naphthenate can be used as an accelerator for peroxide. Other suitable bioactive materials are disclosed in U.S. Pat. No. 5,928,611 to Leung and U.S. patent application Ser. No. 08/920,876, filed Aug. 29, 1997, Ser. No. 09/430,176 filed Oct. 29, 1999, and Ser. No. 09/430,177, filed Oct. 29, 1999, the entire disclosures of which are incorporated herein by reference.

Other examples of adhesives 100, 101, 102, 103, adhesive initiators 104, and alternate compounds 105 may be found in U.S. application 20040190975 by Goodman et al. which is herein incorporated by reference in its entirety.

Alternate Fluid Application System

Figure 10:
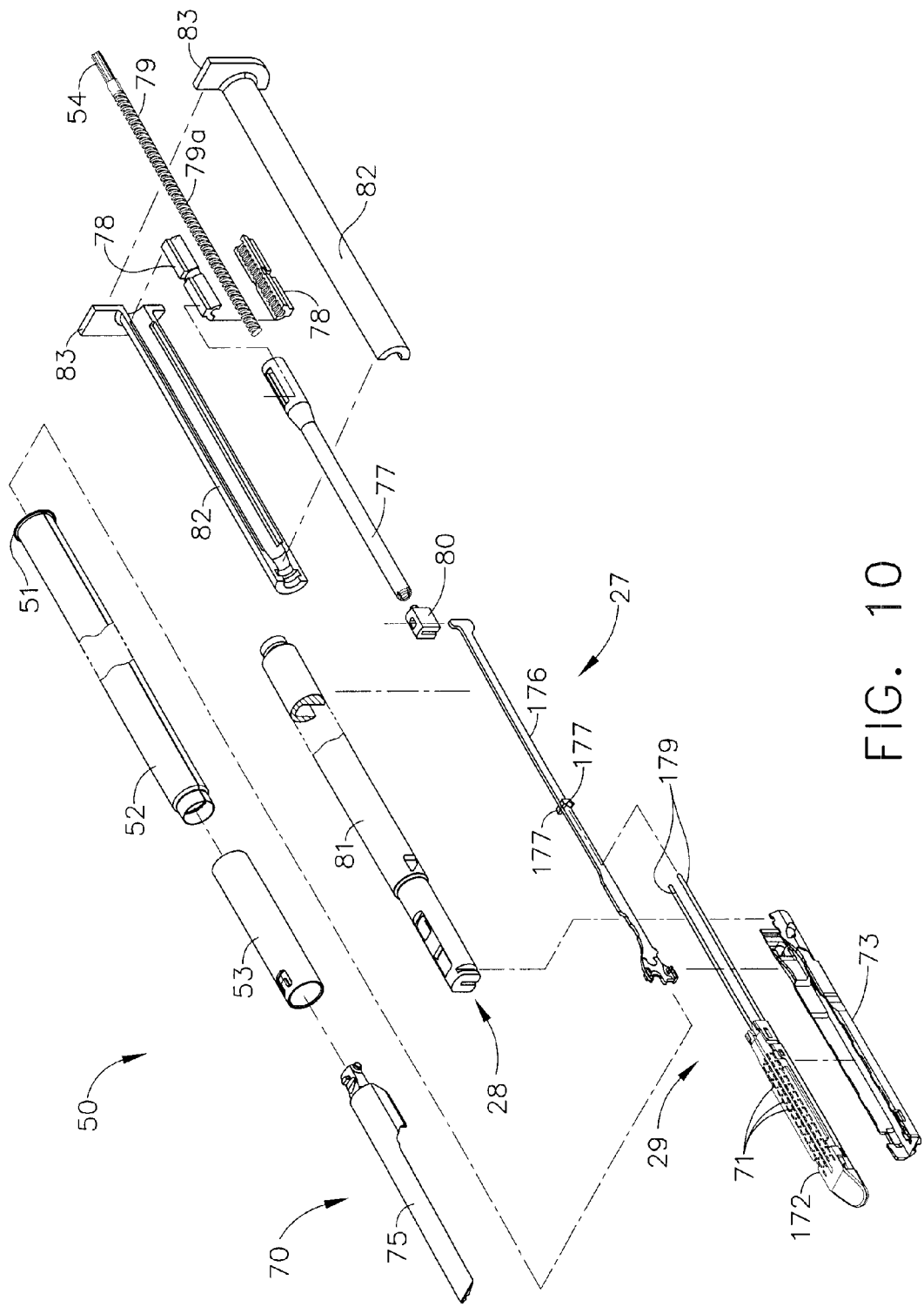
FIG. 10 is an isometric exploded view of a second shaft assembly showing a second fluid application system and second cartridge.

FIGS. 10-17 show an alternate example of an alternate surgical device 125 that can have a cartridge fluid application system 126 with an alternate removable cartridge 172. The alternate removable cartridge 172 could store the adhesive 101 within one or more generally rigid chamber and can use an alternate cylinder and piston system to dispense the adhesive 101 from the cartridge. FIG. 10 is an exploded view of an alternate shaft assembly 150 showing the elements therein with the alternate removable cartridge 172.

In FIG. 10, the alternate shaft assembly 150 uses many of the same elements described previously. For example, the clamping system 26 and the frame system 28 described previously are used. An alternate firing system 127 is shown that can include an alternate knife 176 in combination with the screw shaft 79, the firing shaft 77, and the coupler 78 to operatively engage with the clamping system 26, and frame system 28.

As shown in FIG. 10, the alternate removable cartridge 172 can include at least one flexible and movable push member 179 extending distally therefrom. When the alternate removable cartridge 172 is placed into the shaft assembly 150 of the alternate surgical device 125, the push members 179 can flex and deflect as the alternate removable cartridge 172 is inserted. A proximal end 180 of the push members 179 can operatively engage with sockets 177 extending from the alternate knife 176 when the alternate removable cartridge 172 is fully seated.

Figure 11:
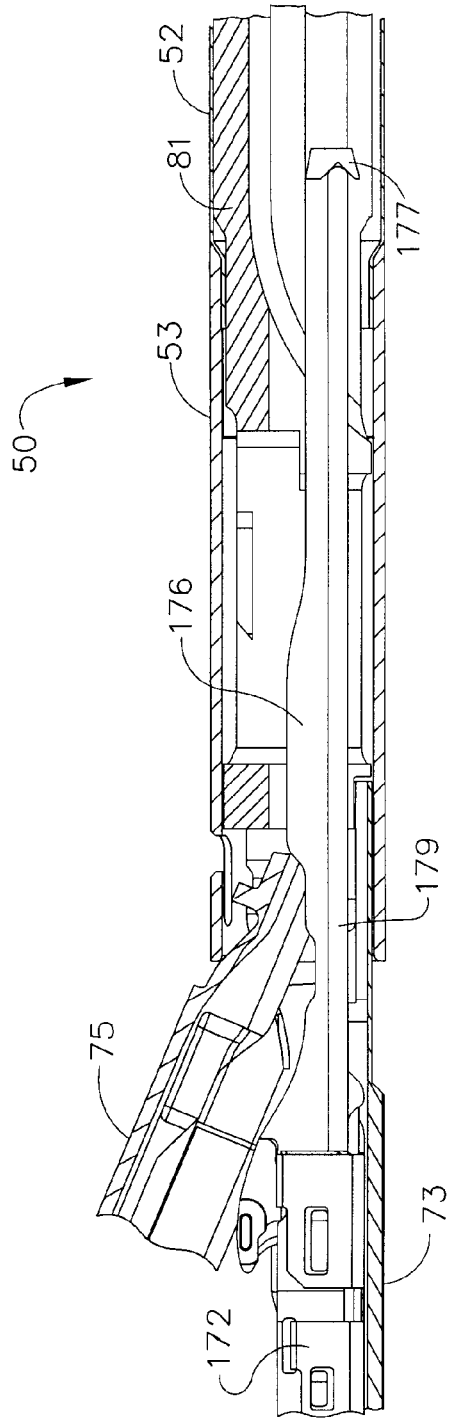
FIG. 11 is a cross sectional end view of the second staple cartridge of FIG. 10 before clamping, cutting, stapling, and applying fluid.

FIG. 11 is a cross sectional view of the alternate shaft assembly 150 showing the alternate removable cartridge 172 fully seated therein. The anvil 75 is shown open and the push members 179 can be operably engaged with the sockets 177 flanking the alternate knife 176.

Figure 12:
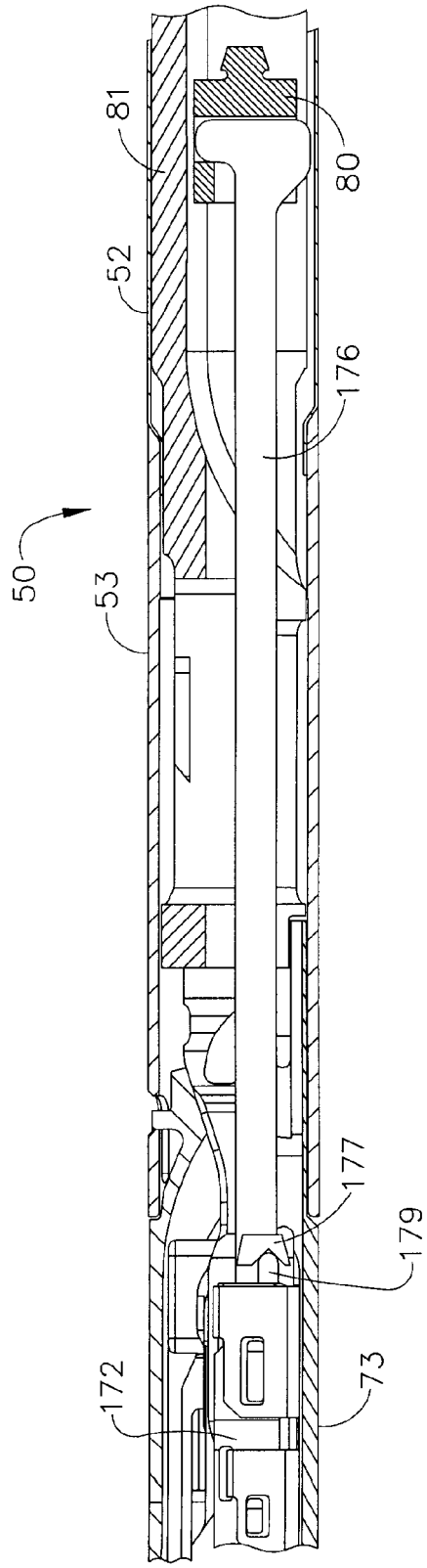
FIG. 12 is a cross sectional side view of the second shaft assembly of FIG. 10 after clamping, cutting, stapling and applying fluid to tissue

In FIG. 12, alternate surgical device 125 has clamped and fired on tissue to move alternate knife 176 distally to form the staples 71 and cut the tissue. This action has moved sockets 177 distally to drive push members 179 into the alternate removable cartridge 172, and can dispense the adhesive 101 from the alternate removable cartridge 172. The alternate removable cartridge 172 will now be described in more detail.

Figure 13:
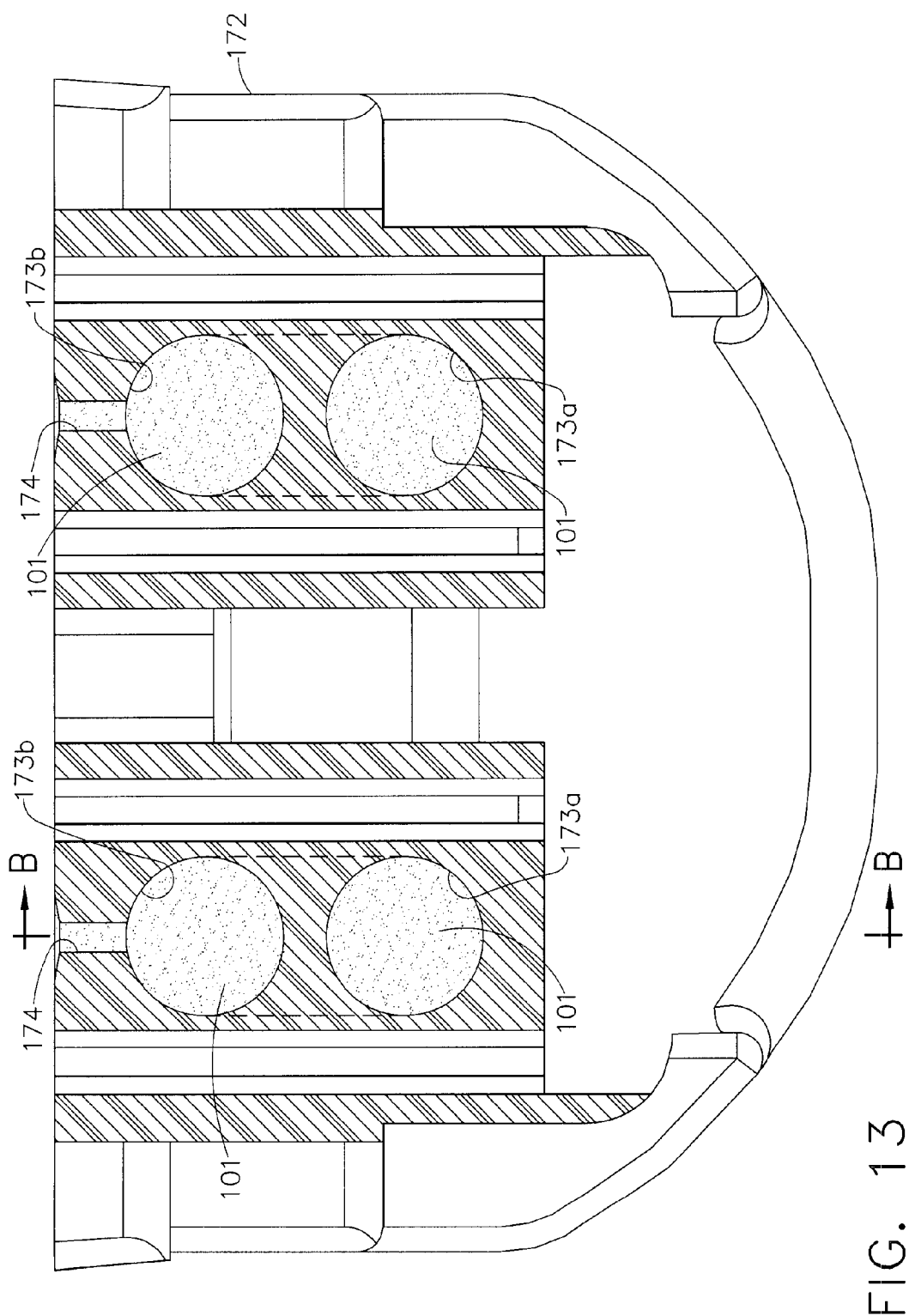
FIG. 13 is a cross sectional end view of the second staple cartridge of FIG. 10 showing the fluid and the second fluid application system therein.

FIG. 13 is a cross-section across the alternate removable cartridge 172 to show the elements therein. As shown, one or more cylinders 173a and 173b can extend longitudinally along the alternate removable cartridge 172 and can operably connect with a plurality of open passageways 174. The one or more cylinders 173a and 173b, and the open passageways 174 may be filled with adhesive 101.

FIGS. 14 and 15 are cross sectional side views of the alternate removable cartridge 172 across cross section B-B of FIG. 13. As shown, the cross section is across one of the pair of one or more cylinders 173a and 173b, and across one row of the plurality of open passageways 174. A piston 175 may be located at the ends of the push members 179 to create a sliding seal with the cylinder 173a. Pushing on push members 179 can move parallel pistons 175 along parallel cylinders 173a to drive adhesive 101 from cylinders 173a, into cylinders 173b and from the open passageways 174. Whereas a dual cylinder single piston design is shown, a single cylinder design operably coupled with open passageways 174 and with a piston 175 is also within the scope of this invention.

Using a piston 175 in a cylinder 173a that feeds cylinder 173b can offer more uniform dispersement of adhesive 101 from open passageways 174 and along the entire length of the removable cartridge 172. During adhesive dispersement, the piston 173 traverses along cylinder 173a and uniformly pressurizes chamber 173b to constantly dispense adhesive 101 from all of the open passageways 174 throughout the entire stroke of piston 175 within cylinder 173a. With a single cylinder design with the piston moving proximal to distal past the plurality of open passageways 174, the initial movement of the piston dispenses adhesive 101 uniformly from all passageways 174. Further movement of the piston past a distalmost passageway 174 stops the flow of adhesive 101 from the distalmost passageway yet continues the flow of adhesive from more distal passageways 174

Vent Cartridge

Figure 16:
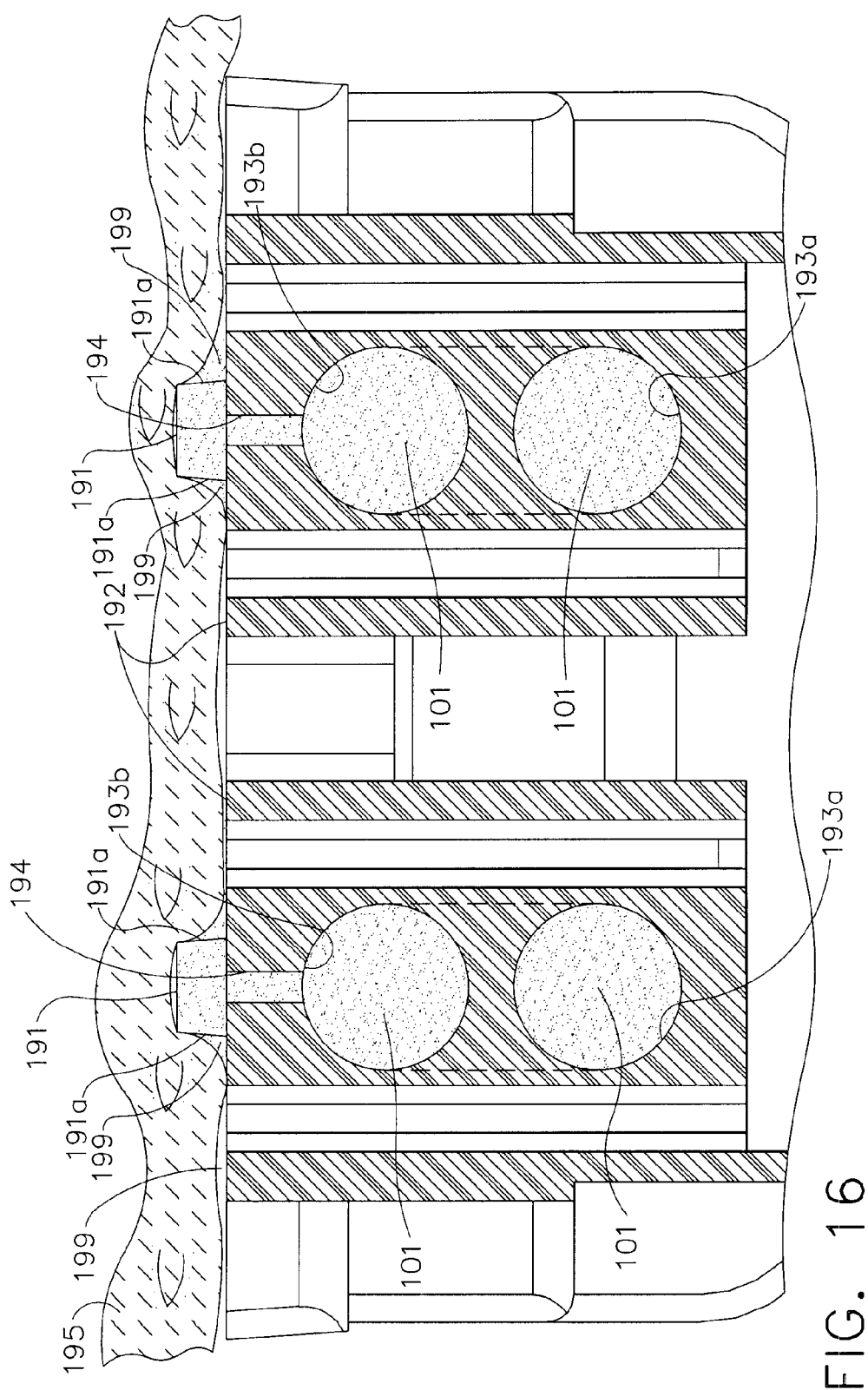
FIG. 16 is a cross sectional end view of a third embodiment of a staple cartridge showing the fluid and the third fluid application system therein and showing a plurality of vents on the cartridge creating gaps with tissue.
Figure 17:
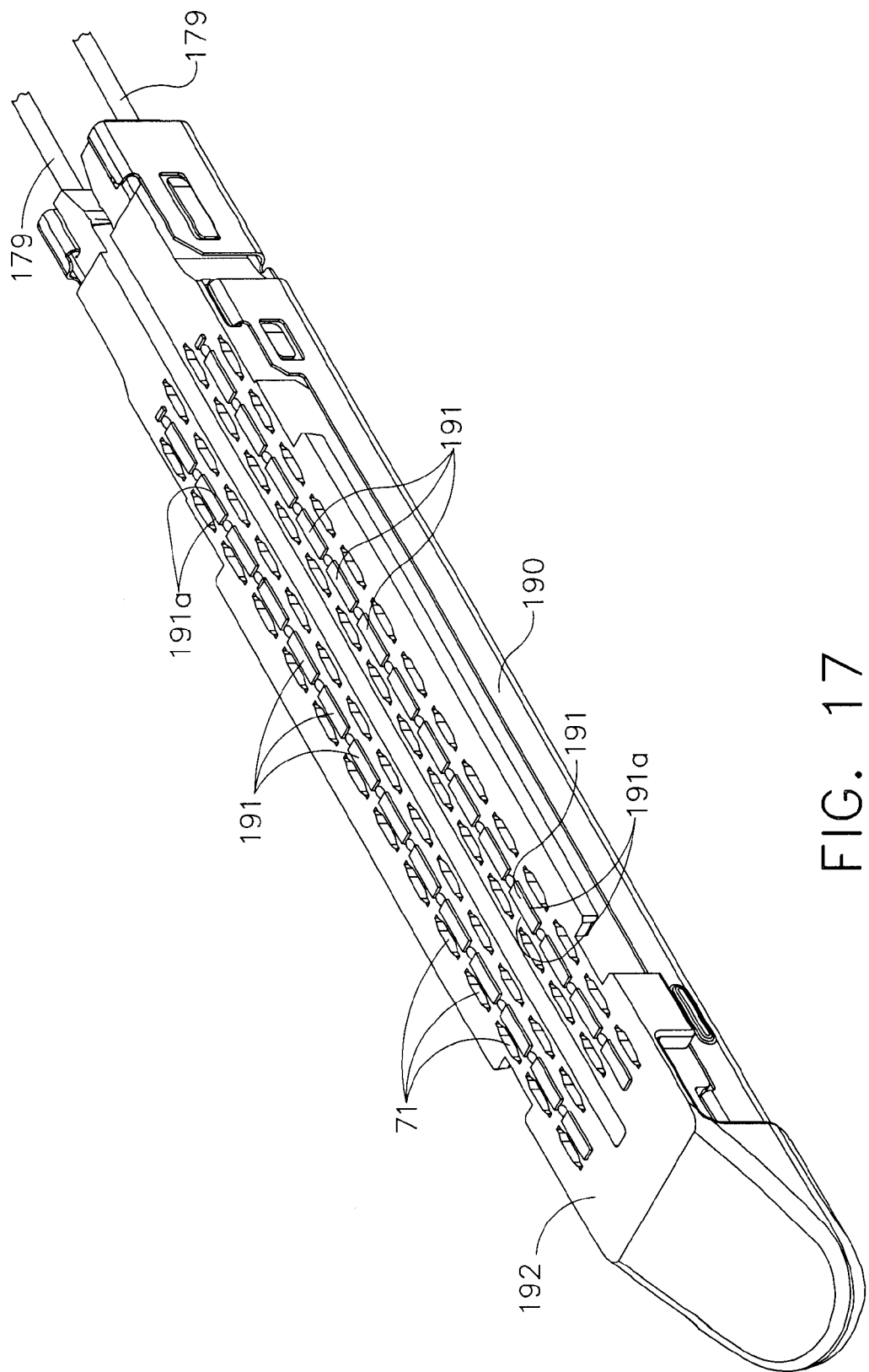
FIG. 17 is an isometric cross sectional view of a third embodiment of a staple cartridge showing the vents of FIG. 16

FIGS. 16 and 17 show an alternate embodiment of a removable cartridge that can contain fasteners such as staples 71, and a fluid 100 such as adhesive 101. In this example, a vent cartridge 190 can have a plurality of vents 191 located over passageways 194 that extend upwards from a tissue clamping surface 192. Vents 191 may have vent openings 191a over a plurality of passageways 194 for the passage of fluid 100 or adhesive 101 therefrom. As shown, a portion of tissue 195 placed across the vents 191 could be tented upwards creating gaps 199 for the adhesive 101 to flow therein. As adhesive 101 is driven through cylinders 193a and 193b and passageways 194, the adhesive 101 can flow laterally out of vent openings 191a. If desired, vent openings 191a can be in any orientation to direct the flow of fluids 100 therefrom. FIG. 17 shows an isometric view of the vent cartridge 190 with vents 191 and vent openings 191a extending above clamping surface 192. Whereas this vent cartridge 190 is shown with the single piston and dual cylinder 173a and 173b design of cartridge 172, vents 191 can be added to any cartridge that can dispense a fluid 100 or an adhesive 101 and fall within the scope of this invention.

Manual Fluid Application System

Figure 18:
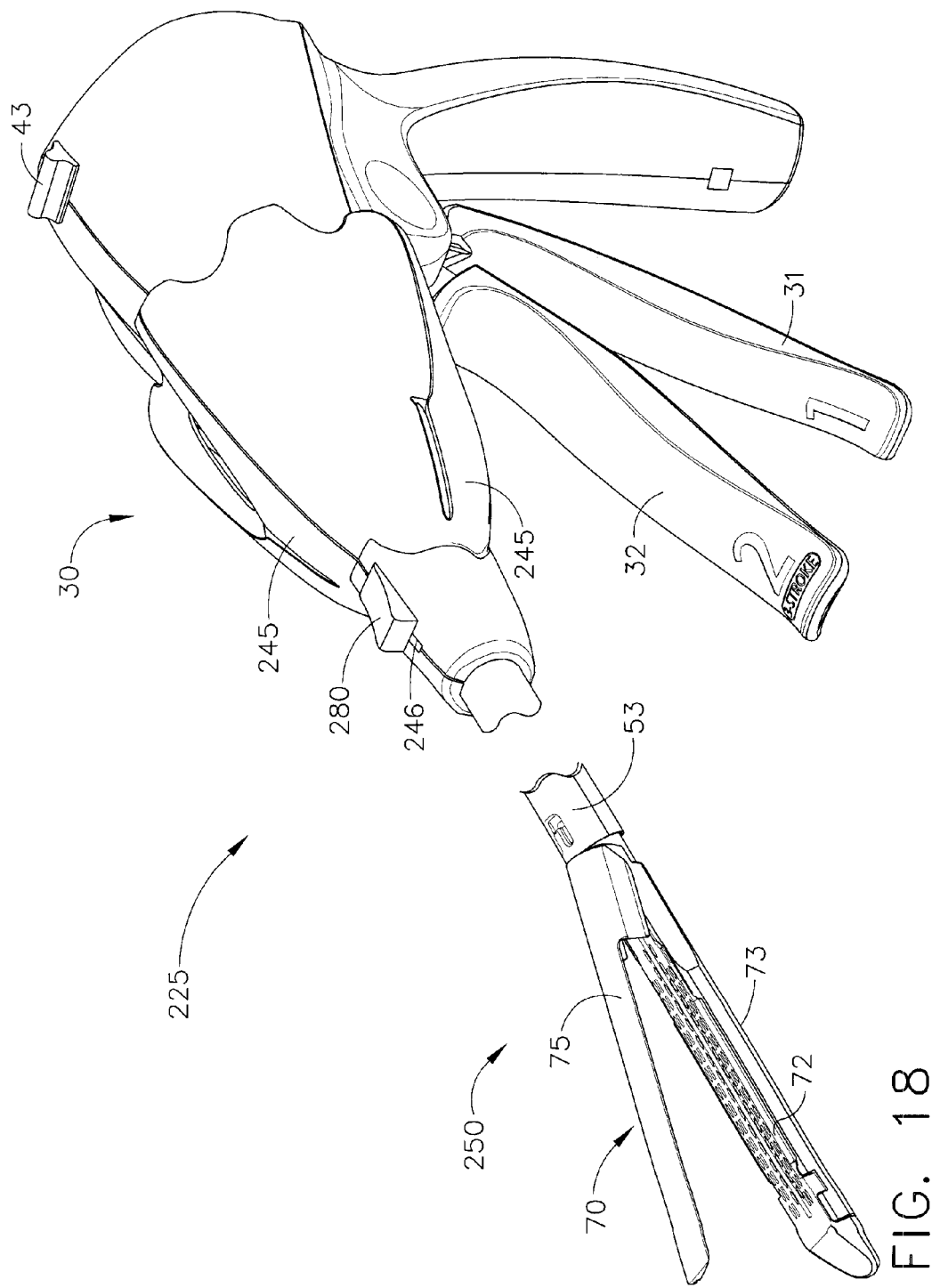
FIG. 18 is an isometric view of another alternate surgical device for clamping, stapling, and cutting tissue, with a manually actuated fluid application system for dispensing fluid onto tissue.
Figure 19:
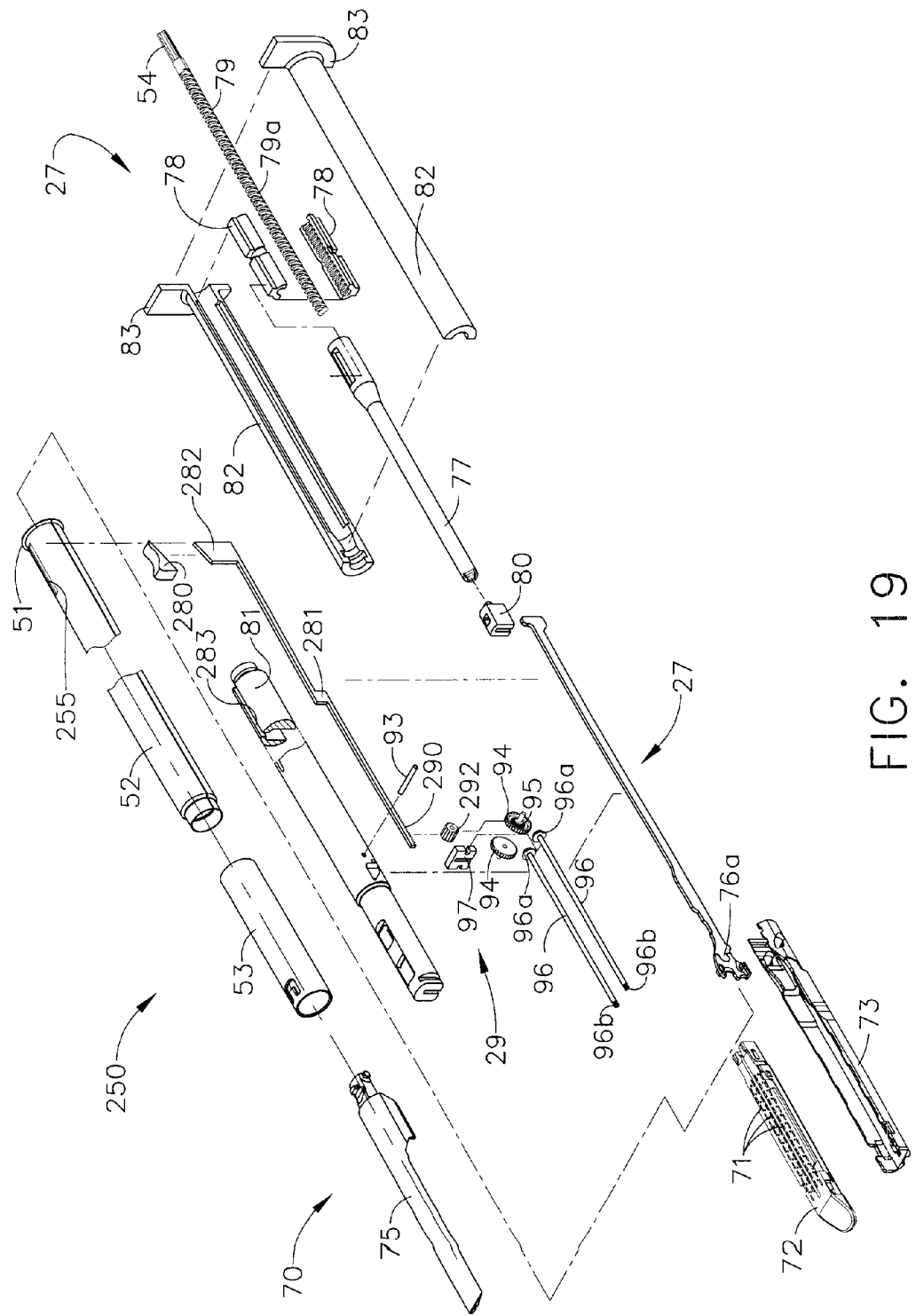
FIG. 19 is an isometric exploded view of a shaft assembly of the alternate surgical device of FIG. 18 showing the manually actuated fluid application system elements.
Figure 20:
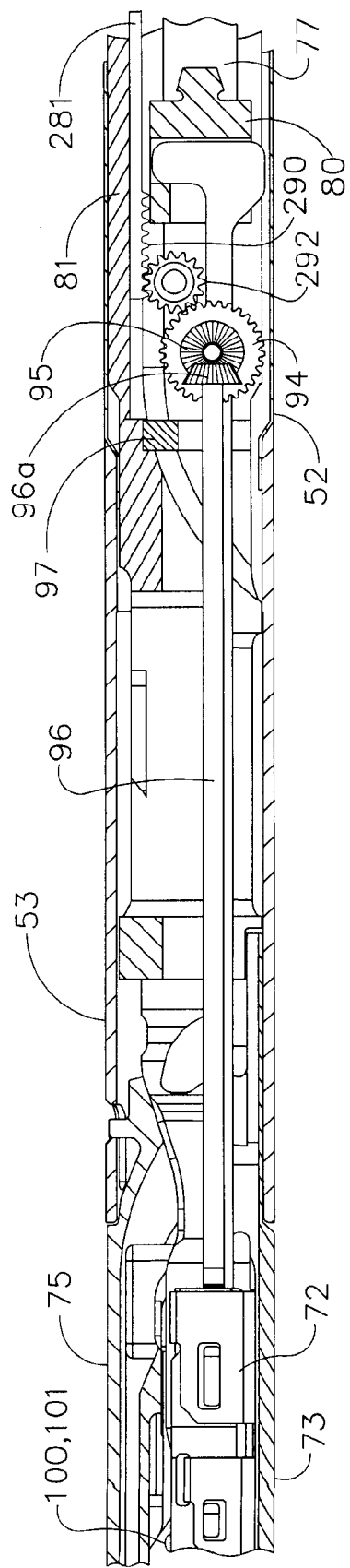
FIG. 20 is a cross sectional side view of the shaft assembly of FIG. 18 after clamping, cutting, stapling tissue and showing the manually actuated fluid application system engaged and applying fluid to tissue.

FIGS. 18-20 show another alternate example of an alternate surgical device 225 having a manual adhesive dispensing system 210 that can be manually activated at any time to dispense a fluid 100 or an adhesive 101 from a cartridge such as cartridge 72. As shown in FIG. 18, the alternate surgical device 225 has a handle mechanism 30 described above that can be modified to operably couple to a manual shaft assembly 250. The clamping system 26, the firing system 27, and the frame system 28 are modified and/or adapted to manually dispense a fluid from a cartridge 72 by actuation of a control 280. In FIG. 18, a manual knob 245 can have a longitudinal slot 246 therein below control 280 for longitudinal travel of the control 280. The modifications to the shaft assembly 250 will now be described.

FIG. 19 shows an exploded view of the shaft assembly 250. Clamping system 26 can include a longitudinal control slot 255 within the closure tube 50 about the flange 51. A longitudinal second slot 283 may be located within the distal frame portion 81 to align with the control slot 255 in the closure tube 50 when shaft assembly 250 is assembled. The fluid application system 29 could have gear 91, 92 replaced with a manual gear 292 and knife 76 can be modified to remove the gear rack 90 removed therefrom. The removal of the gear rack 90 from the knife 76 can enable the fluid 100 or adhesive 101 to be dispensed manually by actuation of control 280. An actuation member 280 is provided on the handle assembly 30 to operably couple the actuation member 280 to the fluid application system 29 via the drive gear 292. A tab 282 of the actuation member 281 is slidingly received within second slot 283 in the distal frame portion 81 and within slot 255 in closure tube 52. A manual gear rack 290 is located on the distal underside of actuation member 281. Tab 282 is received in control 280 and longitudinal movement of control 280 results in longitudinal movement of actuation member 281 within second slot 283 in the distal frame portion 81, longitudinal movement within slot 255 in closure tube 52, and brings manual gear rack 290 into operative engagement with manual gear 192 of the fluid application system 29.

FIG. 20 is a cross sectional view of the shaft assembly 250 with the clamping system 26 clamped on tissue, the firing system 27 has fired to form staples 71 in tissue and the knife 76a has cut the tissue between the innermost rows of formed staples 71. The manual adhesive dispensing system 210 is shown partially actuated by moving the control 280 distally. Distal movement of the control 280 has moved actuation member 281 distally within shaft assembly 250 and has just engaged the manual gear rack 290 with the manual gear 292 of the manual adhesive dispensing system 210. The engagement of the manual gear rack 290 with the manual gear 292 can dispense adhesive from adhesive passageways 112 in cartridge 72. The above manual adhesive dispensing system 210 is merely an example and is not meant to limit the scope of this invention. For example, a rotary screw system, an electric system, a pneumatic system, a hydraulic system or any other system could be operatively attached to a manually operatable control such that movement of the control in any direction could dispense adhesives 101 or fluids 100 from a cartridge.

The manual adhesive dispensing system 210 offers several exemplary advantages over automatically dispensed adhesive dispensing systems in that the surgeon can dispense the fluid onto tissue at any time. For example, the surgeon could choose to dispense the fluid 100 from the cartridge 72 prior to clamping on tissue, on clamped tissue prior to stapling and cutting, during stapling and cutting, after stapling and cutting, or even after releasing the cut and stapled tissue. This added flexibility offers many new and novel surgical options such as, but not limited to reclamping to seal bleeders with adhesive after cutting and stapling tissue, coating the tissue with adhesive 100 so that the staples 71 pass through adhesive 101 when fired, applying drugs at any time and the like.

Another alternate embodiment of the present disclosure can be to create an adhesive cartridge 372 (not shown) for use in a surgical stapling device 25 or a circular stapler that solely contains dispensable adhesive to fasten tissue, and does not include staples or other surgical fasteners. By way of example such a cartridge can be created from the previously described removable cartridge 72 by depopulating the cartridge 72 of staples 71. Alternately, byway of example, an entirely unique adhesive cartridge 372a (not shown) containing adhesive and no provision to hold or fire staples 71 could be provided. Such a cartridge could include the wiper 114 or any other adhesive dispensing system described above. With an adhesive cartridge, the endoscopic instrument 25 can be used to clamp onto tissue for the required time and can transect the tissue and apply adhesive 100 to the transected tissue.

Alternately, in yet another embodiment of the present disclosure, the firing mechanism 27 could be altered to provide an alternate firing mechanism 427 (not shown) that can provide multiple firings of adhesive from the adhesive cartridges 372 and 372a. For example, rather than dispensing the entire contents from the adhesive cartridges 372 and 372a, a part of the total angular rotation of the wiper blades 114 in the cartridges adhesive cartridges 372 and 372a could be used for each firing of the endoscopic instrument 25. The alternate firing mechanism 427 can be made from firing mechanism 27 by reducing the length of gear rack 90 to reduce rotation of the wiper blade 114 for each stroke, and providing a one way clutch 273 (not shown) between gear 91 and the drive gears 92. The one way clutch 273 would engage to drive the gears 92 as gear 91 rotates from the rack 90 moving distally, and slips when the rack 90 retracts. The slipping prevent gears 92 from rotating as the rack 90 retracts at the end of the firing stroke and prevents wiper blade 114 from returning to the initial position. The next firing stroke would disperse an additional amount of adhesive 100 by rotating the wiper blade 114 an additional amount.

In another alternate embodiment of the present disclosure, a Radio Frequency (RF) electrode 500 (not shown) could be incorporated into the anvil 75 and used in combination with the adhesive cartridges 372, 372a and the alternate firing mechanism 427. Such an endocutter 525 can clamp on tissue, can apply RF energy to tissue, can cut the tissue and can dispense adhesive 100 onto the tissue. The combination of RF and adhesives can provide additional hemostasis and reinforcement to the cut and coagulated tissue. An example of a RF electrode arrangement that can be incorporated into anvil 75 is shown in U.S. patent application Ser. No. 11/154,326 to Yates et al. which is hereby incorporated by reference in its entirety.

In yet another alternate embodiment of the present disclosure, a surgical stapling device 25 can be provided that enables multiple firings of staples from the cartridge and multiple applications of adhesives 100 from the staple cartridge. This can be accomplished by placing a plurality of gear racks 90 onto the knife 72 of the alternate firing mechanism 427 to enable multiple applications of adhesive from a cartridge such as cartridge 72. Thus, for example, a first partial firing of one half of the staples 71 from cartridge 72 will apply adhesive 100 to tissue. The knife can be retracted and the surgical device 25 reclamped on tissue and fired to dispense the second half of the adhesive 100 and the second half of the staples 71 from the cartridge 72.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, whereas an embodiment is disclosed for providing multiple firings of staples 71 and adhesive 100 from the cartridge 72, any one of a number of alternate firing mechanism 572 can be provided such as dispensing one row of staples at a time in combination with adhesive 100.

What is claimed is:

1. A surgical stapling device for clamping and stapling tissue comprising:
    a) a shaft defining a longitudinal axis;
    b) a first clamping jaw and a second clamping jaw extending from a distal end of the shaft to clamp tissue therebetween, the second clamping jaw movable from an open position for the reception of tissue to a closed position to clamp tissue between the first clamping jaw and the second clamping jaw;
    c) a removable cartridge mounted in the first clamping jaw and having a tissue clamping surface thereon, the removable cartridge comprising:
        i) a plurality of staples and staple ejection members therein,
        ii) a fluid, and
        iii) a cartridge dispensing system for dispensing the fluid from the clamping surface of the removable cartridge, the cartridge dispensing system having at least one rigid chamber defined by the removable cartridge and configured to be inaccessible to the staples and staple ejection members, the at least one rigid chamber being further configured with a substantially rigid rotatable member therein configured to pump fluid from the rigid chamber, the cartridge dispensing system further comprising a plurality of rigid fluid passageways operably connecting the at least one rigid chamber with the tissue clamping surface, the at least one rigid chamber and the plurality of rigid fluid passageways containing the fluid therein stored in direct contact with the removable cartridge and the substantially rigid rotatable member, and separate from contact with the plurality of staples and staple ejection members, wherein the substantially rigid rotatable member is rotatable about a rotation axis, wherein the rotation axis is parallel to the longitudinal axis;
    d) a firing system within the surgical stapling device having a translating member, wherein the translating member is translatable along a direction that is parallel to the longitudinal axis, wherein the translating member operably couples with the staples and staple ejection members when the firing system is actuated to eject the plurality of staples from the removable cartridge into clamped tissue and form the staples against the second clamping jaw, wherein the substantially rigid rotatable member is removably coupled with the translating member by a dog clutch mechanism; and
    e) a fluid application system is at least partially contained within the shaft and operably coupling with the substantially rigid rotatable member in the removable cartridge and with the translating member when the removable cartridge is mounted in the first clamping jaw, wherein the fluid application system is operable to convert longitudinal translation of the translating member into rotation of the substantially rigid rotatable member about the axis of rotation, wherein when the fluid application system is actuated, the substantially rigid rotatable member of the cartridge dispensing system is rotated about the rotation axis in response to translation of the translating member along the direction that is parallel to the longitudinal axis and fluid is dispensed from the removable cartridge onto tissue.

2. The surgical device of claim 1 wherein the fluid is one or more selected from a group consisting of a polymerizable monomer adhesive, a polymerizable 1,1-disubstituted ethylene monomer adhesive, a cyanoacrylate formulation adhesive, a drug, an adhesive initiator, a desiccant, a clotting agent, an image enhancing agent, and a therapeutic agent.

3. The surgical device of claim 2 wherein the removable cartridge includes a removable cartridge cover to seal the fluid passageways from fluid loss, wherein the removable cartridge cover is one or more selected from the group consisting of:
    a) a removable tape;
    b) a meltable film; and
    c) a removable pouch.

4. The surgical device of claim 2 wherein the cartridge dispensing system further comprises a wiper blade driven by the substantially rigid rotatable member, wherein rotation of the rotatable member and wiper blade dispenses the fluid from the removable cartridge.

5. The surgical device of claim 1 wherein the rotatable member has one or more seals to prevent egress of the fluid therefrom.

6. The surgical device of claim 1 wherein the translating member of the firing system has a gear rack that operably couples with the rotatable member of the removable cartridge during firing to rotate the rotatable member and to dispense fluid from the removable cartridge with at least a portion of the firing stroke.

7. The surgical device of claim 6 wherein one or more actuations of the firing system dispense the fluid from the removable cartridge.

8. The surgical device of claim 4 wherein the dog clutch mechanism is operable to couple the rotatable wiper blade of the cartridge dispensing system with the translating member when the removable cartridge is placed within the first clamping jaw, wherein the dog clutch mechanism is further operable to decouple the rotatable wiper blade of the cartridge dispensing system from the translating member when the removable cartridge is removed from the first clamping jaw.

9. The surgical device of claim 1 wherein the fluid application system has an operator actuatable control operably coupled to the rotatable member and wiper blade of the cartridge dispensing system when the removable cartridge is placed within the first clamping jaw, wherein when the surgeon manually moves the control, fluid is dispensed from the fluid passageways and onto tissue between the first clamping jaw and the second clamping jaw.

10. The surgical device of claim 9 wherein an operator actuatable control has a gear rack that operably couples with the rotatable member to dispense the fluid from the removable cartridge.

11. A removable fluid cartridge for use in a surgical stapling device for clamping and firing on tissue, the removable fluid cartridge comprising;
  a) a fluid cartridge body having a tissue clamping surface, a hollow chamber, and a plurality of passageways operably connecting the hollow chamber to the tissue clamping surface, the fluid cartridge body further comprising a staple driver configured to eject a staple from the tissue clamping surface when the surgical stapling device is fired, wherein fluid cartridge body further comprises a first moving member movable along a slot formed in the cartridge body, wherein the slot extends in a longitudinal direction;
  b) a fluid within the hollow chamber and the plurality of passageways of the fluid cartridge body, the fluid stored in contact with the fluid cartridge body and isolated from contact with the staple driver and staple by the fluid cartridge body; and
  c) a fluid dispensing system within the cartridge body for dispensing the fluid from the plurality of passageways, wherein when the fluid cartridge is installed into the surgical stapling device, the fluid dispensing system is operably coupled with a staple firing system of the surgical stapling device such that firing the surgical stapling device moves the first moving member longitudinally along the slot in the fluid cartridge body and into contact with the staple driver to form the staple, wherein the fluid dispensing system further comprises at least one second moving member positioned in contact with the fluid in the chamber, the at least one second moving member being rotatable within the chamber to dispense the fluid onto tissue from the plurality of passageways, wherein the at least one second moving member is rotatable about a rotation axis that extends in the longitudinal direction, wherein the first moving member is isolated from contact with the fluid by the fluid cartridge body, wherein the first moving member is also isolated from contact with the at least one second moving member by the fluid cartridge body;
  wherein the fluid cartridge is operable to translate the first moving member in the longitudinal direction while simultaneously rotating the at least one second moving member about the rotation axis that extends in the longitudinal direction, to simultaneously form at least one staple and dispense the fluid from the plurality of passageways.

12. The surgical device of claim 11 wherein the fluid is one or more selected from a group consisting of a polymerizable monomer adhesive, a polymerizable 1,1-disubstituted ethylene monomer adhesive, a cyanoacrylate formulation adhesive, a drug, an adhesive initiator, a desiccant, a clotting agent, an image enhancing agent, and a therapeutic agent.

13. The surgical device of claim 11 wherein the fluid can be dispensed by one or more firing strokes of the staple firing system.

14. The surgical stapling device of claim 1 wherein the surgical stapling device includes one or more RF electrodes for clamping on tissue and applying RF energy to the clamped tissue.

\* \* \* \* \*

UNITED STATES PATENT AND TRADEMARK OFFICE
CERTIFICATE OF CORRECTION

PATENT NO. : 7,721,930 B2
APPLICATION NO. : 11/558524
DATED : May 25, 2010
INVENTOR(S) : Robert H. McKenna et al.

It is certified that error appears in the above-identified patent and that said Letters Patent is hereby corrected as shown below:

Title page Item [73]

The Assignee, reads "Thicon Endo-Surgery, Inc.,"

which should be deleted and replaced with

"Ethicon Endo-Surgery, Inc.,".

Signed and Sealed this

Third Day of August, 2010

David J. Kappos
*Director of the United States Patent and Trademark Office*